US009192735B2

(12) United States Patent
Gillespie

(10) Patent No.: US 9,192,735 B2
(45) Date of Patent: Nov. 24, 2015

(54) FAN UNIT WITH BYPASS VENT HOLES

(75) Inventor: Christopher David Gillespie, Stouffville (CA)

(73) Assignee: Fisher & Paykel Healthcare Limited, Auckland (NZ)

( * ) Notice: Subject to any disclaimer, the term of this patent is extended or adjusted under 35 U.S.C. 154(b) by 1312 days.

(21) Appl. No.: 12/739,809

(22) PCT Filed: Oct. 30, 2008

(86) PCT No.: PCT/NZ2008/000289
§ 371 (c)(1),
(2), (4) Date: Jun. 8, 2011

(87) PCT Pub. No.: WO2009/058032
PCT Pub. Date: May 7, 2009

(65) Prior Publication Data
US 2011/0226245 A1    Sep. 22, 2011

(30) Foreign Application Priority Data
Oct. 30, 2007 (NZ) ........................................ 563002

(51) Int. Cl.
*A62B 18/08* (2006.01)
*A61M 16/00* (2006.01)
*A61M 15/00* (2006.01)
*A61M 16/10* (2006.01)
*A61M 16/16* (2006.01)

(52) U.S. Cl.
CPC ....... *A61M 16/0066* (2013.01); *A61M 16/0069* (2014.02); *A61M 16/109* (2014.02); *A61M 16/1095* (2014.02); *A61M 16/16* (2013.01); *A61M 2205/42* (2013.01)

(58) Field of Classification Search
None
See application file for complete search history.

(56) References Cited

U.S. PATENT DOCUMENTS

| 5,577,496 | A  | * | 11/1996 | Blackwood et al. | ..... 128/201.25 |
| 6,123,074 | A  |   | 9/2000  | Hete et al.      |                  |
| 6,182,657 | B1 | * | 2/2001  | Brydon et al.    | ........ 128/205.24 |

(Continued)

FOREIGN PATENT DOCUMENTS

| EP | 1275412 | A2 |   | 1/2003 |           |
| GB | 2192136 |    | * | 1/1988 | ...... A61M 16/16 |

(Continued)

OTHER PUBLICATIONS

Japanese Examination Report; dated May 12, 2012; 3 pages.

(Continued)

*Primary Examiner* — Jackie T Ho
*Assistant Examiner* — Eric Bryant
(74) *Attorney, Agent, or Firm* — Knobbe, Martens, Olson & Bear, LLP

(57) ABSTRACT

A fan unit which in use forms part of a gases supply unit, the gases supply unit suitable for use as part of a system for providing heated humidified gases to a user, the fan unit having a casing that has an inlet aperture and an outlet passage, the outlet passage including an exit aperture, the fan unit also including a fan which is located inside the casing and which is adapted for connection to a motor to drive rotation of the fan in use, the fan drawing gases into the casing via the inlet aperture, and forcing these gases out of the casing via the outlet passage as a gases stream, the outlet passage further including at least one bypass vent hole independent of the exit aperture and arranged at an angle to the path of the gases stream through the outlet passage.

32 Claims, 13 Drawing Sheets

(56) References Cited

U.S. PATENT DOCUMENTS

| | | | |
|---|---|---|---|
| 6,526,974 | B1 | 3/2003 | Brydon et al. |
| 6,662,803 | B2 | 12/2003 | Gradon et al. |
| 6,881,033 | B2 | 4/2005 | Makinson |
| 7,014,422 | B2 * | 3/2006 | Hancock ............... 415/204 |
| 7,037,084 | B2 * | 5/2006 | King ...................... 417/53 |
| 7,111,624 | B2 | 9/2006 | Thudor et al. |
| 7,128,069 | B2 | 10/2006 | Farrugia et al. |
| 7,137,388 | B2 * | 11/2006 | Virr et al. ............ 128/203.17 |
| 2003/0108441 | A1 | 6/2003 | Mackie |
| 2004/0255948 | A1 * | 12/2004 | Smith et al. ........... 128/206.15 |
| 2005/0016535 | A1 | 1/2005 | Smith et al. |
| 2005/0166919 | A1 * | 8/2005 | Kates ................... 128/203.26 |
| 2007/0089743 | A1 * | 4/2007 | Hoffman .............. 128/204.18 |
| 2009/0301485 | A1 * | 12/2009 | Kenyon et al. ........ 128/204.18 |

FOREIGN PATENT DOCUMENTS

| | | |
|---|---|---|
| GB | 2192136 | 1/2010 |
| JP | S64-500088 | 1/1989 |
| JP | H11-514259 | 12/1999 |
| JP | 2007-512047 | 5/2007 |
| JP | 2009-513192 | 4/2009 |
| WO | WO 2004/052438 | 6/2004 |
| WO | WO2004112873 | 12/2004 |

OTHER PUBLICATIONS

International Search Report, Feb. 29, 2010.
Written Opinion, PCT/NZ2008/000289, dated Feb. 2009; 6 pages.
Examination Report; dated Feb. 8, 2012; 2 pages.

* cited by examiner

FAN UNIT WITH BYPASS VENT HOLES

This application is a United States National Phase filing of PCT/NZ2008/000289, having an International filing date of Oct. 30, 2008 which was published in English on May 7, 2009 under International Publication Number WO 2009/058032 which claims the priority of New Zealand 563002, filed on Oct. 30, 2007. These applications are hereby incorporated by reference in their entirety.

BACKGROUND OF THE INVENTION

1. Field of the Invention

This invention relates to a gases supply and gases humidification apparatus, particularly but not solely for providing respiratory assistance to patients or users who require a supply of gas at positive pressure for the treatment of diseases such as Obstructive Sleep Apnea (OSA), snoring, or Chronic Obstructive Pulmonary Disease (COPD) and the like. In particular, this invention relates to a compressor or blower for use in a gases supply apparatus which in use is integral with the gases supply apparatus.

2. Summary of the Prior Art

Devices or systems for providing a humidified gases flow to a patient for therapeutic purposes are well known in the art. Systems for providing therapy of this type, for example CPAP therapy, have a structure where gases at the required pressure are delivered from a blower (also known as a compressor, an assisted breathing unit, a fan unit, a flow generator or a pressure generator) to a humidifier chamber downstream from the blower. As the gases are passed through the heated, humidified air in the humidifier chamber, they become saturated with water vapour. The gases are then delivered to a user or patient downstream from the humidifier, via a gases conduit.

Humidified gases can be delivered to a user from a modular system that has been assembled from separate units (that is, a system where the humidifier chamber/heater and the breathing unit/blower are separate items) connected in series via conduits. A schematic view of a user 1 receiving air from a known (prior art) modular assisted breathing unit and humidifier system is shown in FIG. 1. Pressurised air is provided from an assisted breathing unit or blower 2a via a connector conduit 10 to a humidifier chamber 4a. Humidified, heated and pressurised gases exit the humidifier chamber 4a via a user conduit 3, and are provided to the patient or user 1 via a user interface 5.

It is becoming more common for integrated blower/humidifier systems to be used. A typical integrated system consists of a main blower or assisted breathing unit which provides a pressurised gases flow, and a humidifier unit that mates with or is otherwise rigidly connected to the blower unit. This mating occurs for example by a slide-on or push connection, so that the humidifier is held firmly in place on the main blower unit. A schematic view of the user 1 receiving air from a known, prior art integrated blower/humidifier unit 6 is shown in FIG. 2. The system operates in the same manner as the modular system shown in FIG. 1, except that humidifier chamber 4b has been integrated with the blower unit to form the integrated unit 6.

The user interface 5 shown in FIGS. 1 and 2 is a nasal mask, covering the nose of the user 1. However, it should be noted that in systems of these types, a mask that covers both the mouth and nose, a full face mask, a nasal cannula, or any other suitable user interface could be substituted for the nasal mask shown. A mouth-only interface or oral mask could also be used. Also, the patient or user end of the conduit can be connected to a tracheostomy fitting, or an endotracheal intubation.

U.S. Pat. No. 7,111,624 includes a detailed description of an integrated system. A 'slide-on' water chamber is connected to a blower unit in use. A variation of this design is a slide-on or clip-on design where the chamber is enclosed inside a portion of the integrated unit in use. An example of this type of design is shown in WO 2004/112873, which describes a blower, or flow generator 50, and an associated humidifier 150.

For these systems, the most common mode of operation is as follows: air is drawn by the blower through an inlet into the casing which surrounds and encloses at least the blower portion of the system. The blower pressurises the air stream from the flow generator outlet and passes this into the humidifier chamber. The air stream is heated and humidified in the humidifier chamber, and exits the humidifier chamber via an outlet. A flexible hose or conduit is connected either directly or indirectly to the humidifier outlet, and the heated, humidified gases are passed to a user via the conduit. This is shown schematically in FIG. 2.

Impeller type fans or blowers are most commonly used in breathing systems of this type. An impeller blade unit is contained within an impeller housing. The impeller blade unit is connected to a drive of some form by a central spindle. A typical impeller housing is shown in FIGS. 3 and 4. A typical rotating impeller blade unit which in use is located inside the housing is shown in FIGS. 5 and 6. Air is drawn into the centre of the impeller unit through an aperture, and is then forced outwards from the centre of the housing towards an exit passage (usually located to one side of the housing) by the blades of the rotating impeller unit. An impeller blower suitable for use with a breathing system is described in U.S. Pat. No. 6,881,033.

Generally, domestic users receive treatment for sleep apnea or similar. It is most common for a nasal mask, or a mask that covers both the mouth and nose, to be used. If a nasal mask is used, it is common to strap or tape the mouth closed, so that the use of the system is effective (mouth leak and the associated pressure drop are substantially reduced or eliminated). For the range of flows dictated by the user's breathing, the CPAP device pressure generator provides a flow of gases at a substantially constant pressure. The pressure can usually be adjusted before use, or during use, either by a user, or a medical professional who sets up the system. Systems that provide variable pressure during use are also known—for example BiPAP machines that provide two levels of pressure: One for inhalation (IPAP) and a lower pressure during the exhalation phase (EPAP).

A person using a breathing assistance apparatus will inhale and exhale as part of their breathing cycle. As the user exhales, they are exhaling against the incoming gases stream provided by the blower. It is well-known in this field of technology to add a one-way or bias valve to the system, on or close to the mask or interface. A mask vent is described in U.S. Pat. No. 6,662,803. This allows exhaled air to be vented to atmosphere.

A mask vent of different design is described in EP 1275412.

U.S. Pat. No. 6,123,074 discloses a system where the mask includes an exhaust port, and where pressure in the breathing system is constantly monitored and a pressure controller downstream of the flow generator (between the mask and the flow generator) acts to maintain a constant pressure within the conduit.

U.S. Pat. No. 6,526,974 discloses a CPAP device where the size of the inlet to the blower or flow generator can be varied, or where the size of the inlet is automatically varied, in response to the needs of the user. An exhalation path is also provided.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

DISCLOSURE OF THE INVENTION

It is an object of the present invention to provide a breathing assistance apparatus which goes some way to overcoming the abovementioned disadvantages or which at least provides the public or industry with a useful choice.

Accordingly, the invention may broadly be said to consist in a fan unit which in use forms part of a gases supply unit suitable for use as part of a system for providing heated humidified gases to a user, said fan unit comprising:
  a casing having an inlet aperture and an outlet passage, said outlet passage including an exit aperture,
  a fan located inside said casing and adapted for connection to a motor to drive rotation of said fan in use, so that in use said fan draws gases into said casing via said inlet aperture, and forces said gases out of said casing via said outlet passage as a gases stream,
  and wherein said outlet passage includes at least one vent hole, independent of said-exit aperture and arranged at an angle to the path of said gases stream through said outlet passage.

Preferably said outlet passage and said at least one vent hole are configured so that if the outlet of said outlet passage is substantially blocked, the flow in use through said vent hole or holes matches the flow through said outlet passage at which the onset of surge would occur in a substantially similar, substantially blocked outlet passage without a vent hole or holes.

Preferably said exit aperture is larger than the cross-sectional area of any one of the individual vent hole or holes by approximately three orders of magnitude.

Preferably said exit aperture is larger than total cross-sectional area of said vent hole or holes by approximately one to two orders of magnitude.

Preferably said angle of said at least one vent hole or holes to said path of said gases stream is substantially perpendicular.

Preferably said outlet passage includes a plurality of said vent holes.

Preferably the total number of said vent holes is between 65 and 75.

Preferably each of said vent holes is substantially the same size as the others of said vent holes.

Preferably said exit aperture has a cross-sectional area of substantially between 210 mm$^2$ and 270 mm$^2$.

Preferably the cross-sectional area of each of said vent holes on the inner surface of said outlet passage is substantially between 0.22 mm$^2$ and 0.26 mm$^2$.

Preferably the total cross-sectional area of said vent hole or holes on the inner surface of said outlet passage is substantially between 15.00 mm$^2$ and 17.00 mm$^2$.

Preferably said vent hole or holes are formed with a draft of substantially between 5° and 15°.

Even more preferably said vent holes are formed with a draft of 10°.

Preferably said casing has a generally circular form and said outlet passage is tangential to said casing.

Preferably said exit aperture has a generally rectangular cross-section.

Preferably said vent holes are located on two opposed sides of said passage.

Preferably substantially the same number of vent holes are formed on each of said opposed sides.

Preferably said inlet aperture is located on the lower face of said casing in use.

Preferably said inlet aperture is located generally centrally on said casing.

Preferably said fan is an impeller unit.

Preferably said impeller unit includes a spindle, adapted for connection to a motor in use to drive said impeller unit, said spindle passing out of the bottom of said casing.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

A preferred form of the present invention will now be described with reference to the accompanying drawings.

FIG. 7 shows an integrated blower/humidifier which forms part of the present invention, or which the present invention can be used with.

DETAILED DESCRIPTION OF THE PREFERRED EMBODIMENTS

The present invention will be described with reference to a system where the humidifier chamber is integrated with the gases supply unit (also referred to as a respirator unit or blower unit). However, it should be noted that the system is equally applicable to a modular system.

Figure 7:
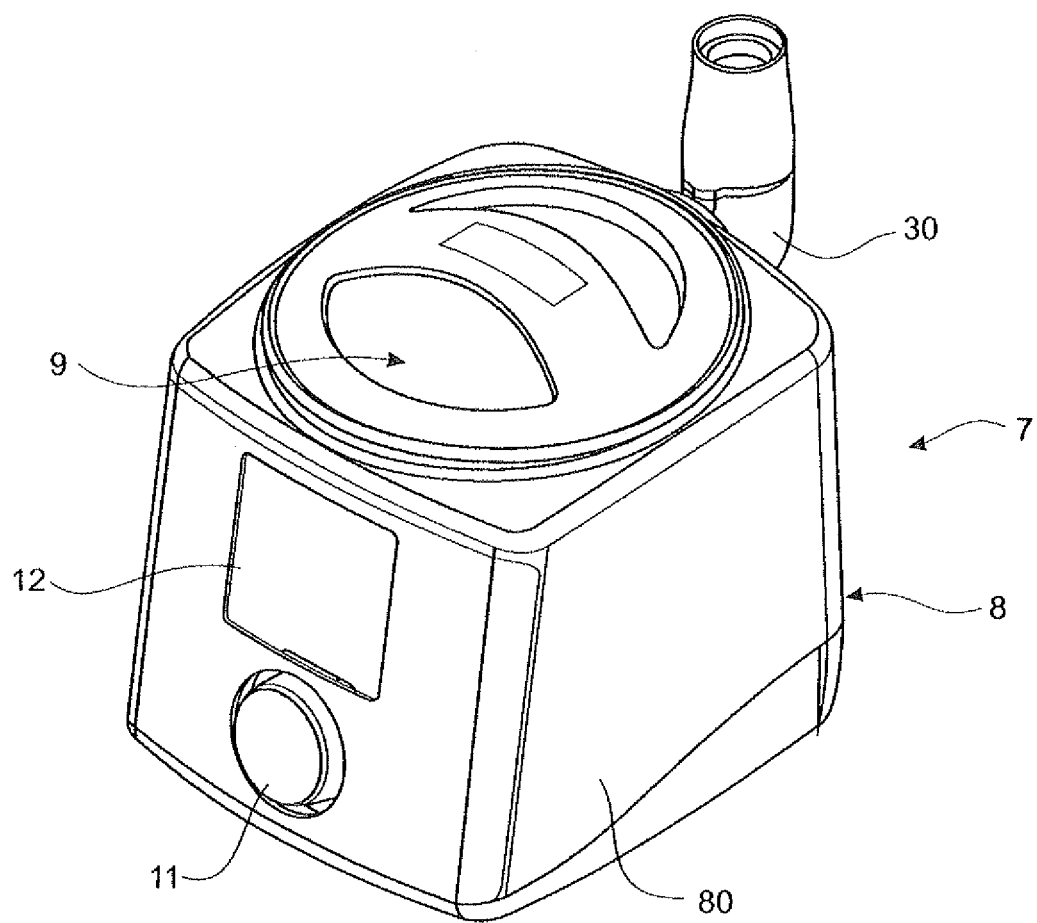

An integrated gases supply unit 7 with which the present invention can be used is shown in FIG. 7. The integrated unit 7 comprises two main parts: a gases supply unit or blower unit 8 and a humidifier unit 9. Humidification unit 9 is partially enclosed within the external shell 80 of the blower unit 8 in use, except for the top of the humidification unit 9. It is not necessary to describe the structure and operation of the humidification unit 9 in detail in order to fully describe the present invention.

Figure 1:
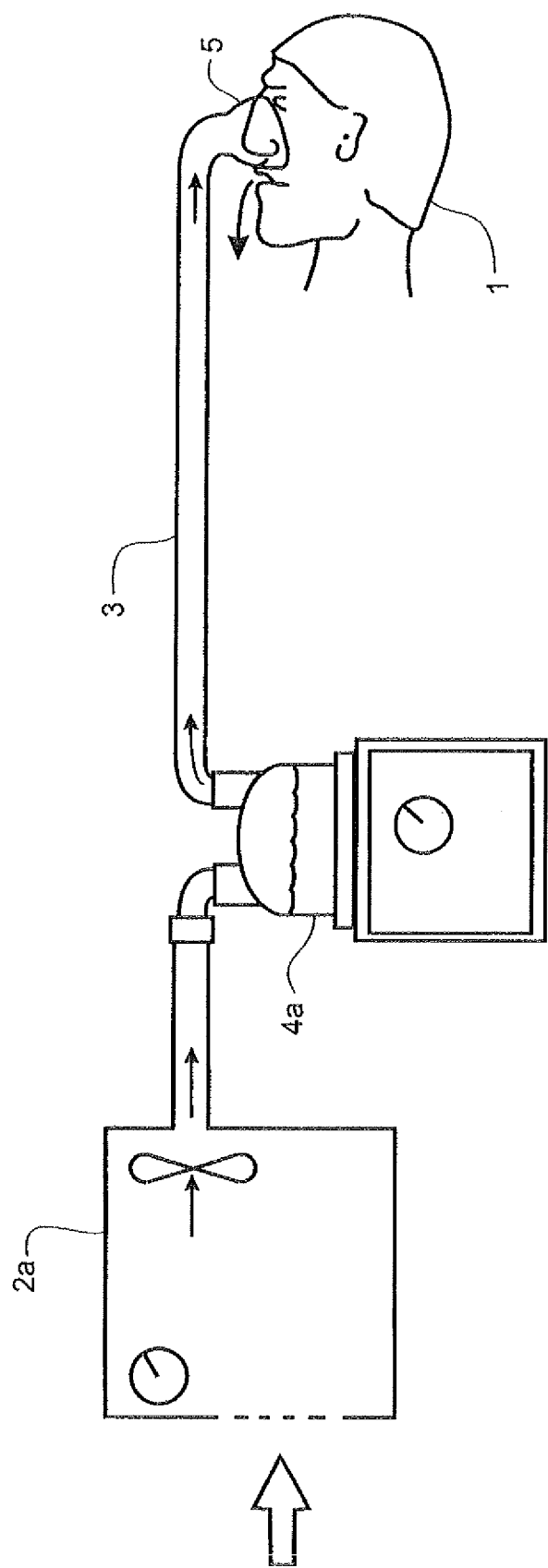
FIG. 1 shows a schematic view of a user receiving humidified air from a modular blower/humidifier system of a known, prior art, type.
Figure 2:
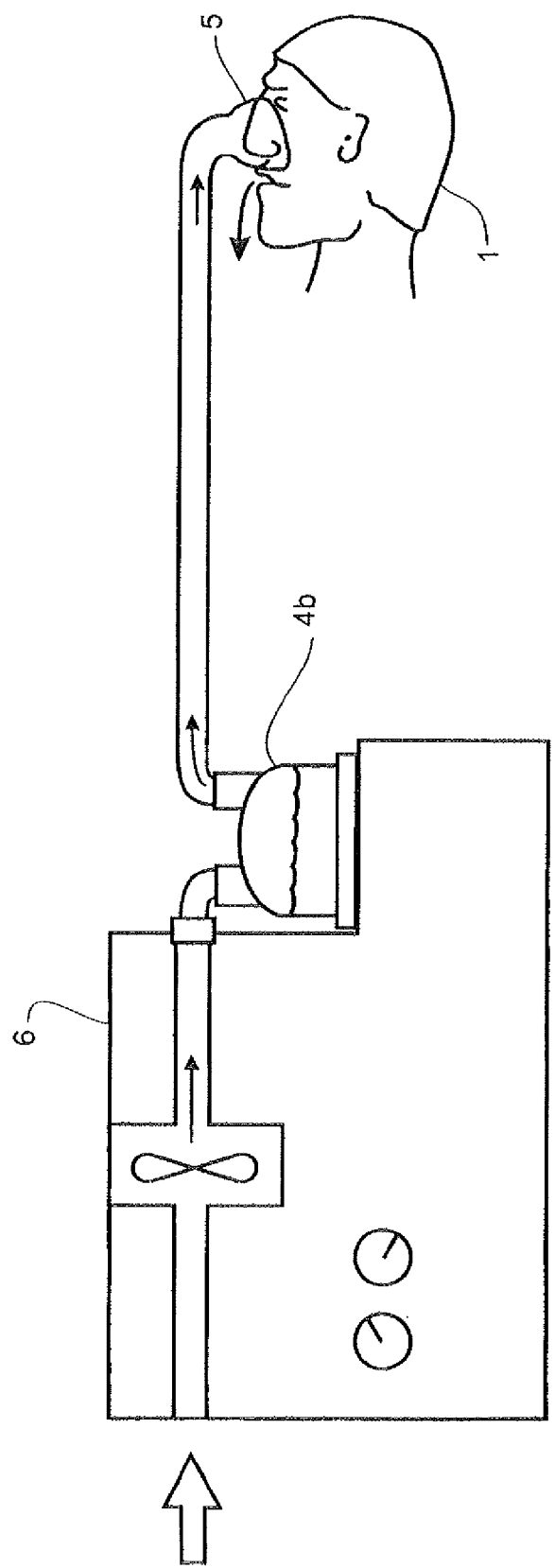
FIG. 2 shows a schematic view of a user receiving humidified air from an integrated blower/humidifier system of a known, prior art, type.
Figure 3:
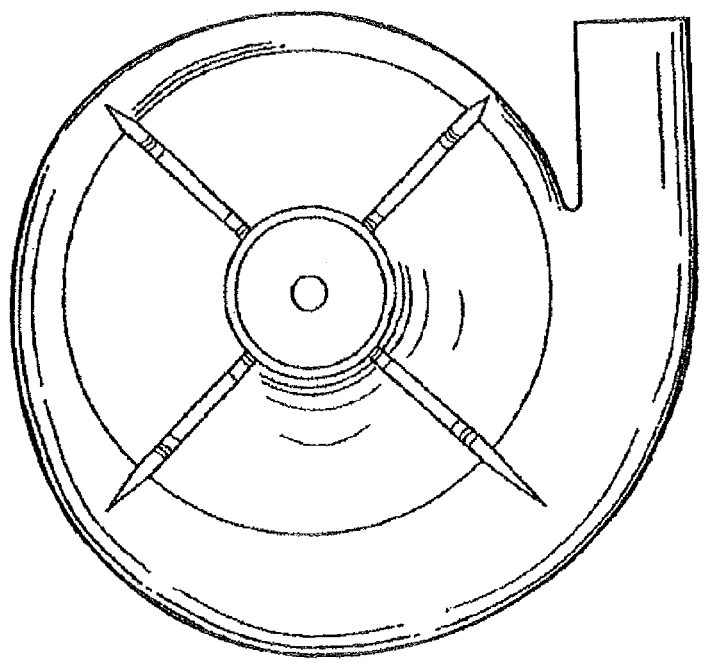
FIG. 3 shows a top view of an impeller casing or fan housing of a known, prior art, type which can be used with the blower or integrated blower/humidifier of FIGS. 1 and 2.
Figure 4:
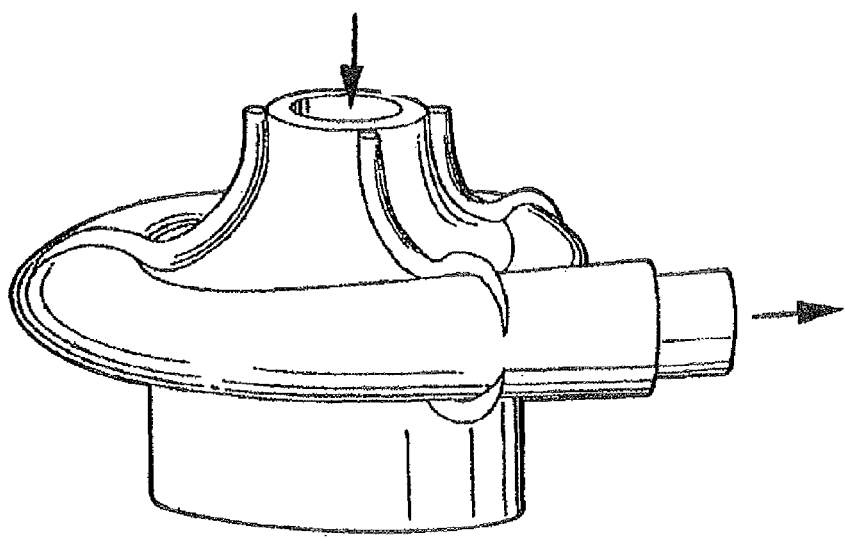
FIG. 4 shows a side view of the fan housing of FIG. 3.
Figure 5:
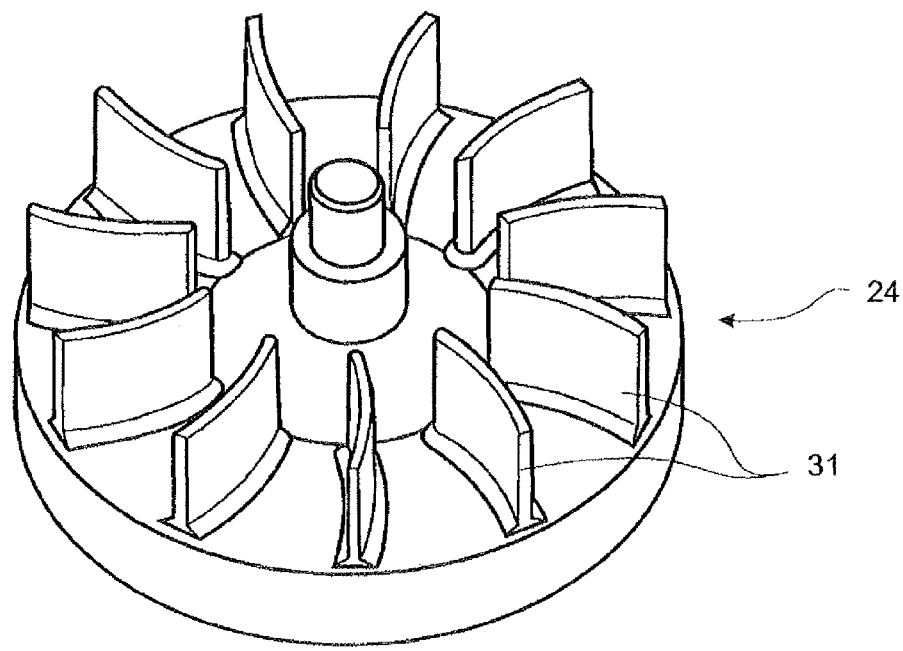
FIG. 5 shows a top perspective view of an impeller unit such as might be used as part of the fan of FIGS. 3 and 4.
Figure 6:
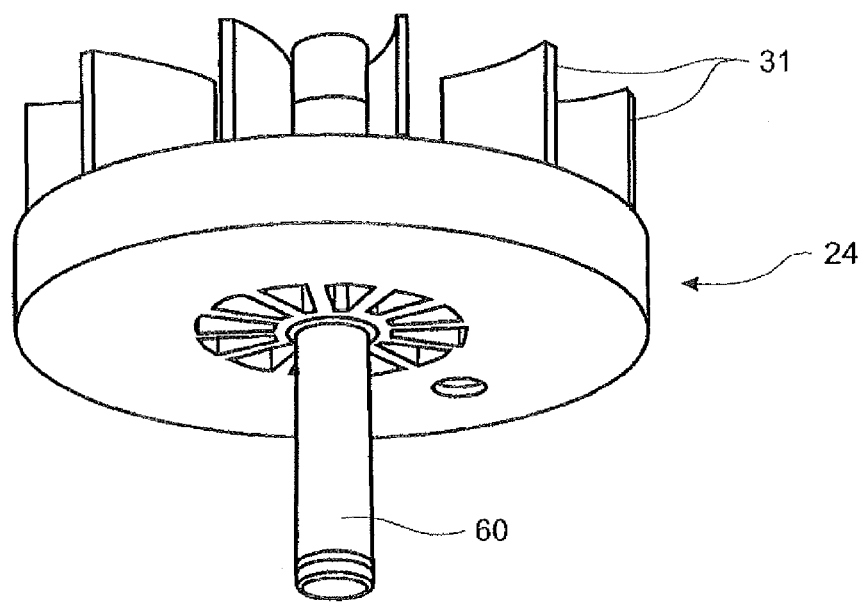
FIG. 6 shows a bottom perspective view of an impeller unit such as might be used as part of the fan of FIGS. 3 and 4.

The body of the gases supply unit 8 has the form of a generally rectangular block with substantially vertical side and rear walls, and a front face that is angled slightly rearwards (all the walls can be angled inwards slightly if required). In the preferred embodiment, the walls, base and top surface are all manufactured and connected as far as possible to minimise the occurrence of seams, and any necessary seams are sealed. As shown in FIG. 3, the gases supply unit 8 includes a control knob 11, located on the lower section of the front face of the gases supply unit 8, with a control display 12 located directly above the knob 11. A patient outlet 30 is shown passing out of the rear wall of the gases supply unit 8. In the preferred embodiment, the free end of the outlet 30 faces upwards for ease of connection. The patient outlet 30 is adapted to allow both pneumatic and electrical connection to one end of a conduit—e.g. conduit 3—running between the integrated unit 7 and a patient interface—e.g. interface 5. An example of the type of connector that can be used and the type of dual connection that can be made is described in U.S. Pat. No. 6,953,354. It should be noted that for the purposes of reading this specification, the patient interface can be thought of as including both the interface 5 and the conduit 3 where it would be appropriate to read it in this manner.

Figure 8:
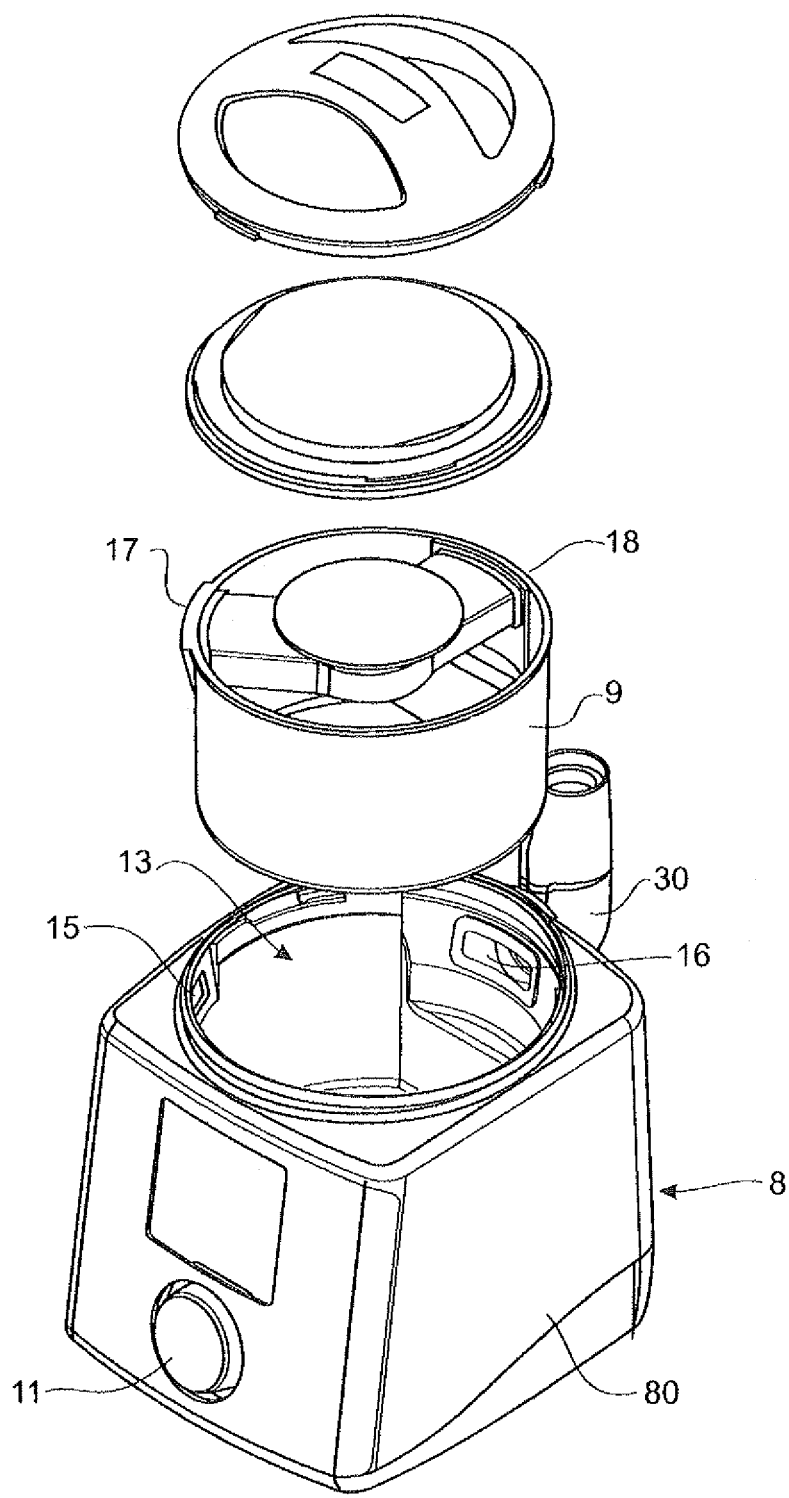
FIG. 8 shows an exploded view of the integrated blower/humidifier of FIG. 7.
Figure 9:
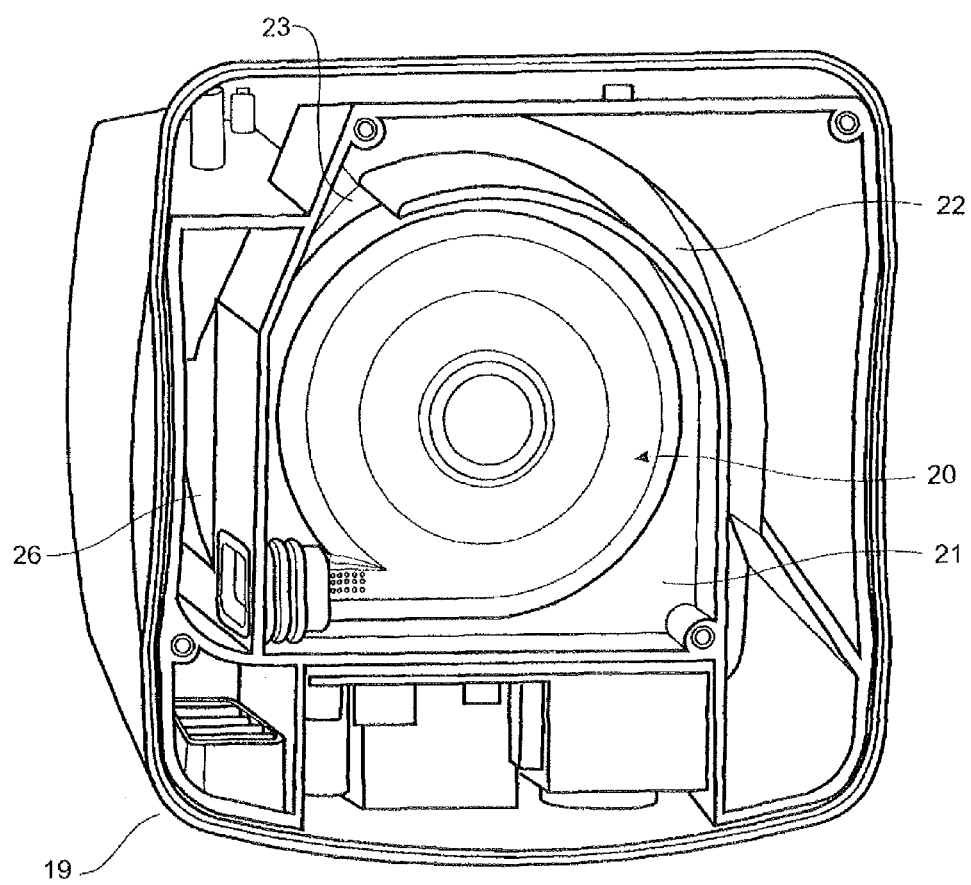
FIG. 9 shows a bottom perspective view of the blower of FIGS. 7 and 8.
Figure 10:
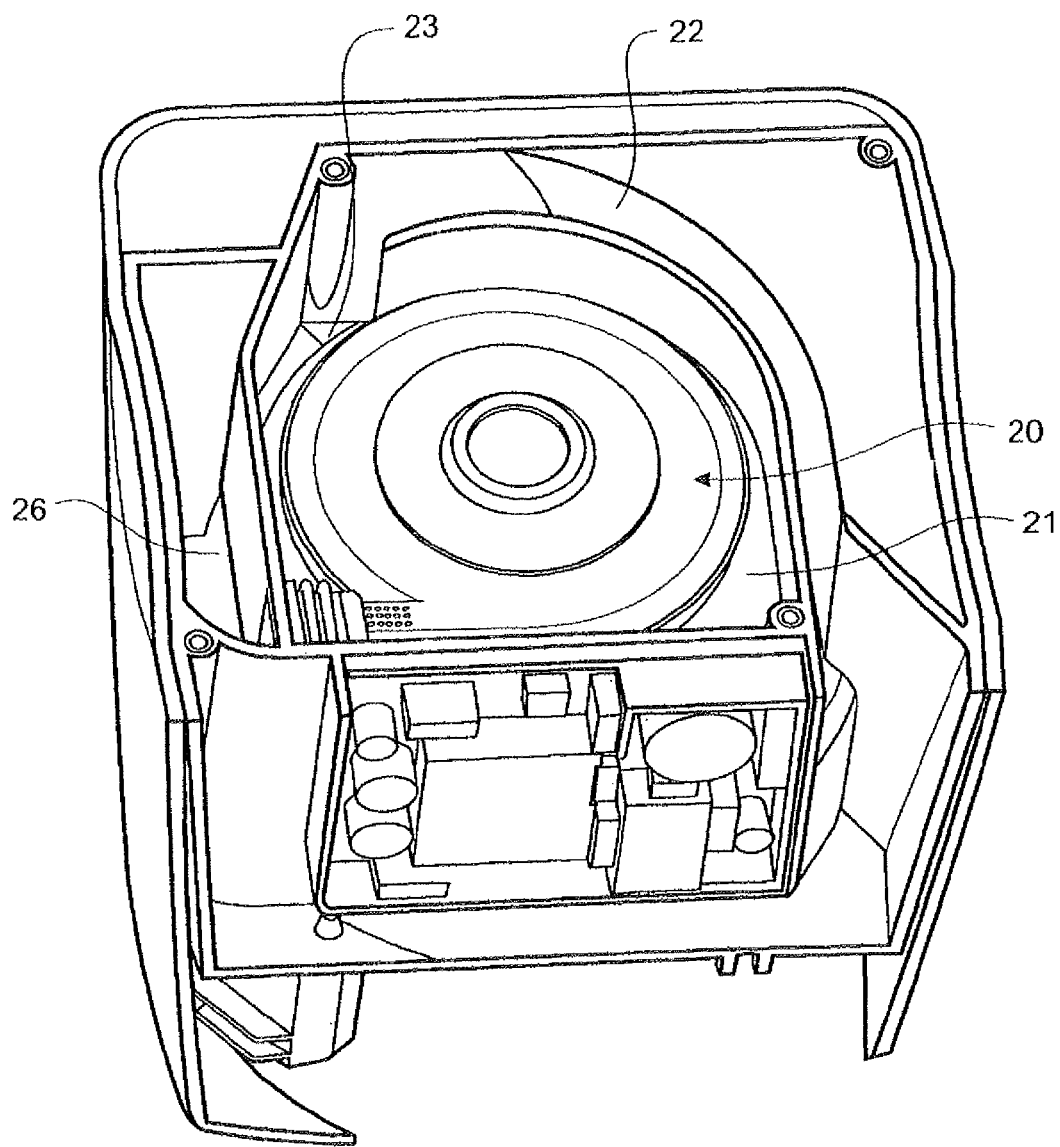
FIG. 10 shows a side bottom perspective view of the blower of FIGS. 7 and 8

The internal structure and components of the gases supply unit 8 will now be described with reference to FIGS. 8, 9 and 10. The gases supply unit 8 includes an enclosing external shell 80 which forms part of, and encloses, the gases supply unit 8. The shell 80 includes internal air passages for ducting air passing through the gases supply unit 8, and also internal recesses, cavities or slots into which componentry of the gases supply unit 8 is located in use. The shell 80 of the gases supply unit 8 is further adapted to include an open-topped compartment 13. In use, humidifier chamber 9 is located within the compartment 13. Blower unit 8 includes a heater base or heater plate (not shown), located at the bottom of the compartment 13. A humidifier inlet aperture 15 and humidifier outlet aperture 16 are located on the wall of the compartment 13, towards the top of the compartment 13. In the preferred embodiment, the inlet and outlet apertures 15, 16 are aligned so as to mate with inlet and outlet humidifier ports 17, 18 located on the humidifier chamber 9, when the system is in use. It should be noted that other forms of humidifier inlet are possible. For example a conduit running between the gases supply unit 8 and e.g. the lid of the humidifier chamber 9. Also, if the humidifier chamber is a separate item (that is, not rigidly connected to the gases supply unit in use), the humidifier inlet aperture 15 will not be connected directly to the humidifier chamber, but will be connected instead to one end of a conduit or similar leading from the humidifier inlet aperture on the gases supply unit, to the humidifier chamber.

Air from atmosphere is drawn into the shell of the gases supply unit 8 through an atmospheric inlet vent 19. This vent 19 can be located wherever is convenient on the external surface of the shell of the gases supply unit 8. In the preferred embodiment, as shown in FIG. 9, the inlet vent 19 is located on the rear face of the shell of the gases supply unit 8, on the right hand side of the rear face (right hand side when looking forwards). In the preferred embodiment, air is drawn in through the inlet vent 19 by means of a fan unit 20 which forms part of the gases supply unit 8, and which is located inside the enclosing external shell of the gases supply unit 8. The fan unit 20 provides a pressurised gases stream for the gases supply unit and therefore the assisted breathing system. The fan unit 20 will be described in more detail below. The air is drawn into the fan unit 20 indirectly, via a curved inlet path 22 formed through the shell of the gases supply unit 8. Path 22 runs from the inlet vent 19 to an aperture 23 formed in the gases supply unit shell 80, the aperture 23 passing into a recess 21 which is formed in the gases supply unit shell 80, in which the fan unit 20 is located.

The gases stream passes through the fan unit 20 to the humidifier inlet aperture 15 as follows: the shell of the gases supply unit 8 includes a chamber or outlet duct 26 which forms at least part of an outlet air path to allow gaseous communication between the fan unit 20 and the humidifier inlet aperture 15. In the preferred embodiment, the outlet duct 26 runs up between the right hand side wall of the gases supply unit 8 (from behind looking forwards) and the front wall, up to the humidifier inlet aperture 15. As shown in FIGS. 9 and 10, air exiting the fan unit 20 enters the duct 26.

In use, air exits the shell of the gases supply unit or blower 8 via the humidifier inlet aperture 15 and enters the humidifier chamber 9. In the preferred form, the humidifier inlet aperture 15 forms an outlet at the end of the duct 26. The gases are humidified and heated in the chamber 9, before passing out of the chamber 9 through the humidifier outlet aperture 16, which is directly or indirectly connected to the patient outlet 30 (it should be noted that the outlet of the humidifier chamber 9 could also be completely separate from the gases supply unit 8). The heated humidified gas is then passed to the user 1 via conduit 3. The patient outlet 30 is adapted to enable pneumatic attachment of the patient conduit 3, and in the preferred embodiment, outlet 30 is also adapted to enable electrical connection via an electrical connector. A combined electrical and pneumatic connection can be useful for example if the conduit 3 is to be heated. Electrical heating of a conduit such as conduit 3 can prevent or minimise the occurrence of condensation within the conduit 3. It should also be noted that the outlet connection does not have to be via the shell of the integrated unit 7. If required, the connection for the conduit 3 could be located directly on an outlet from humidifier chamber 9.

The blower unit 8 in use is set to a user-specified pressure level. The flow rate for the preferred embodiment will vary during use, depending on the users breathing. The power to fan unit 20 can be altered, to change the speed at which the impeller 24 is rotating, and therefore the pressure.

Fan Unit and Air Path

Figure 14:
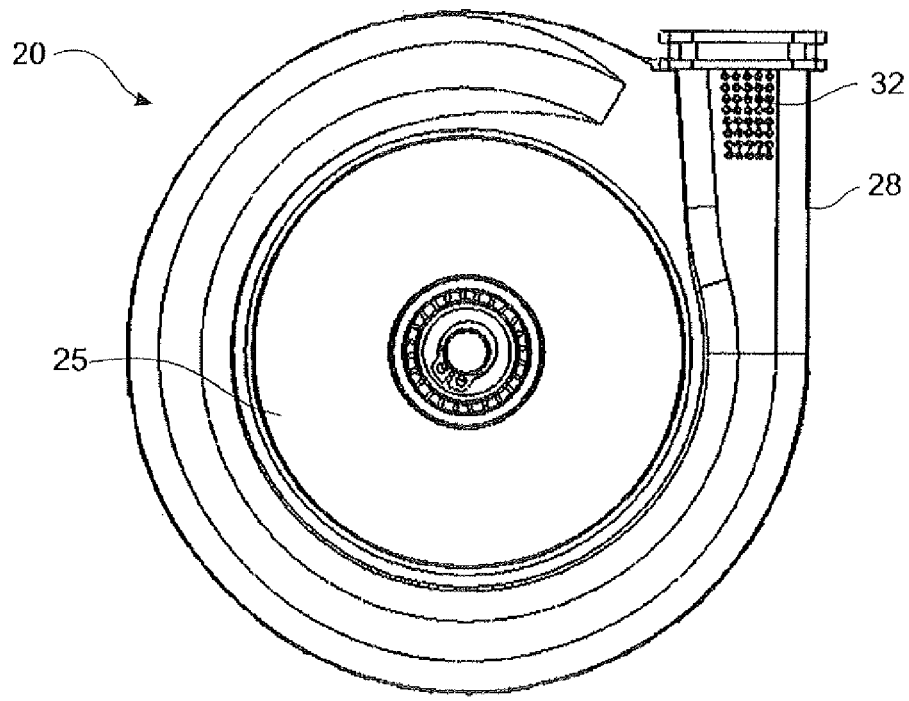
FIG. 14 shows a bottom view of the fan casing of FIGS. 11, 12 and 13.

The structure of the fan unit 20 shall now be described, with particular reference to FIGS. 11 to 16. The fan unit 20 is located in recess 21 of the shell of the gases supply unit 8 in use, as described above with reference to FIGS. 9 and 10. In the preferred form, the fan unit 20 comprises a rotating impeller unit 24 located inside a casing having the form of a snail or scroll casing 25. However, it should be noted that any suitable type of fan or compressor could be used. For example a scroll compressor could be used instead of the impeller unit 24. The compressor off an located inside the casing 25 will be referred to in the general as a 'fan' for the purposes of this specification, and as 'impeller unit 24' for the specific preferred embodiment. It can be seen that the fan unit 20 appears generally circular in plan view, as shown in FIGS. 12 and 14. The fan casing 25 includes an inlet aperture 27. In the preferred form, inlet aperture 27 is a circular hole located in approximately the centre of the lower face of the casing 25 and passing from the outside of the casing to the inside. Air from the inlet path 22 enters the fan casing 25 via the inlet aperture 27. It should be noted that where it would be appropriate to include the aperture 23 and at least part of the recess 21 as part of the air inlet path, the specification should be read as including these elements. The preferred form of the casing 25 of the fan unit 20 also includes an outlet passage 28. In the preferred form, the outlet passage 28 is a short passage formed as an integral part of the casing 25 and aligned substantially circumferentially to the remainder of the generally circular casing 25. A fan casing outlet aperture or exit aperture 29 is located at the outer end of the passage 28. It should be noted that the fan casing exit aperture 29 could be located wherever is convenient on the passage 28 (i.e. it does not have to be at the end of the passage, it could be through the passage wall partway along its length). Exit aperture 29 opens into the duct 26.

The outlet passage 28 forms part of the air path from the fan to the humidifier inlet aperture 15. The fan casing 25 encloses the fan in use, except for the inlet aperture 27 and the exit aperture 29 of the passage 28.

In the preferred embodiment, rotation of the fan unit 20 is driven by a motor (not shown) located outside the casing 25, the fan or impeller unit 24 being adapted for connection to the motor. In the preferred embodiment, the motor is located below the casing 25 in the recess 21, and is an electromagnetic motor. Impeller unit 24 includes a spindle 60 which passes vertically downwards out of the casing 25 to connect with the motor. In use, the motor is powered to rotate the spindle, which causes rotation of the impeller unit 24. In alternative embodiments, the fan could be run indirectly by the motor, for example by gears or similar connecting the fan to the motor, or by magnetic induction or similar. Air or gases are drawn through inlet aperture 27 in the centre of the casing 25, into the centre of the impeller unit 24, and are then forced outwards as a gases stream through the exit aperture 29 of the outlet passage 28 by the impeller blades 31 as the impeller unit 24 rotates. In the preferred form, the fan outlet passage or exit passage 28 has a generally rectangular cross-section, and the exit passage 28 is aligned substantially tangentially to the casing 25. However, the cross-section of the fan outlet passage 28 could be any suitable shape, such as oval, rectangular or circular. The fan outlet passage 28 could also be arranged at any suitable angle to the impeller unit, for example facing radially outwards, or at any suitable angle between tangential and radial. The fan outlet passage 28 causes the gases forced outwards by the impeller unit 24 to coalesce as a fluidic gases stream, and dictates the direction in which the gases stream flows. There will inevitably be some swirling of the gases within the passage. However, the overall path or overall direction of the gases flow will be along the passage from the fan towards the fan casing exit aperture 29.

Figure 17:
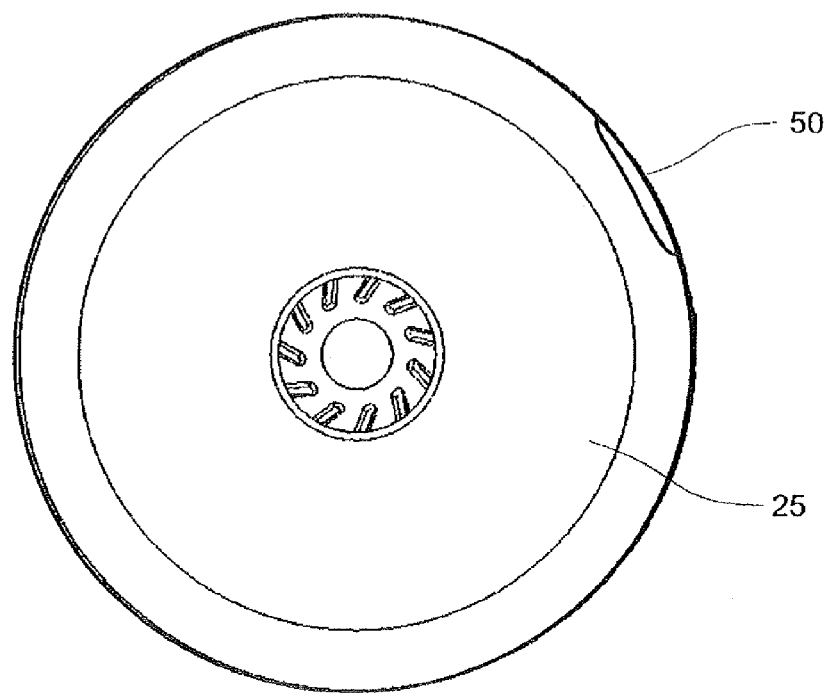
FIG. 17 shows a view from above of an alternative form of fan casing, with an outlet aperture on the circumference of the housing.
Figure 18:
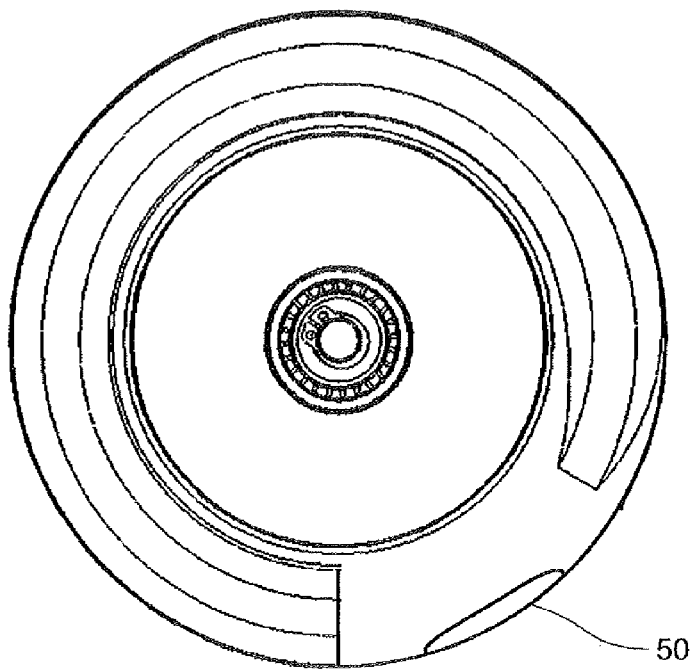
FIG. 18 shows a view from below of an alternative form of fan casing, with an outlet aperture on the circumference of the housing.

In alternative embodiments, and as shown in FIGS. 17 and 18, the fan casing 25 is formed without an integral passage, and has a fan casing outlet aperture 50 on or close to the circumference of the main portion of the casing. In use, this fan casing outlet aperture 50 mates with an outlet passage similar to that described above, but which is either formed as part of the shell 80 of the gases supply unit 8, or as a separate element to both the fan casing 25 and the shell 80 of the gases supply unit 8. If the outlet passage is formed as a separate element, the outlet passage is connected into position during assembly by any suitable mechanism such as glue, friction fit, latches, screws, or similar. In this specification, 'exit aperture' will be used to refer to the exit 29 of the passage 28 (or similar), and 'outlet aperture' will be used to refer to an outlet on or close to the circumference of the main portion of the fan casing 25, which either connects with an integral passage (e.g. passage 28), or which connects with a separate passage, formed as part of the shell of the gases supply unit 8, or formed as a completely separate passage which connects separately to both the fan unit 20 and the shell 80 of the gases supply unit 8. The connection formed in each of these cases is a connection to allow a fluidic connection between the components—so that the gases can pass from one portion of the gases supply unit 8 to another.

The air exiting the impeller unit 24 has both tangential and radial velocity components. The rotational speed of the impeller determines the tangential velocity. The flow drawn by the user will determine the rate at which air exits the impeller, hence the flow rate determines the radial velocity.

A person using a breathing assistance apparatus will inhale and exhale as part of their breathing cycle. As the user exhales, they are exhaling against the incoming gases stream provided by the blower, throttling the gases stream flow. If the gases stream flow from the fan to the user is throttled, then the flow rate diminishes and the radial velocity exiting the impeller decreases. This can cause the flow exiting the impeller to fall back on itself, which causes the impeller unit 24 to stall or surge. Stall or surge can result in high frequency fluctuations in the pressure of the delivered gases stream. The fluctuations can be felt by the user through the gases stream and can cause audible noise, both of which are disturbing for a user. The fluctuations can also introduce vibration into mechanical structures of the system that can cause additional noise that is disturbing for a user.

Surprisingly, it has been found that the addition of bypass vent holes to the fan unit 20 helps to prevent the onset of flow instability, and most surprisingly, at the same time allows a flow rate through the fan housing 25 and the impeller 24 to be maintained (i.e. the overall flow rate is not negatively impacted by the addition of the bypass vent holes). At least a portion of the flow exiting the fan or impeller 24 is diverted through the vent holes instead of stopping when it is choked.

The preferred form of bypass vent holes on the fan unit are described below.

Figure 19:
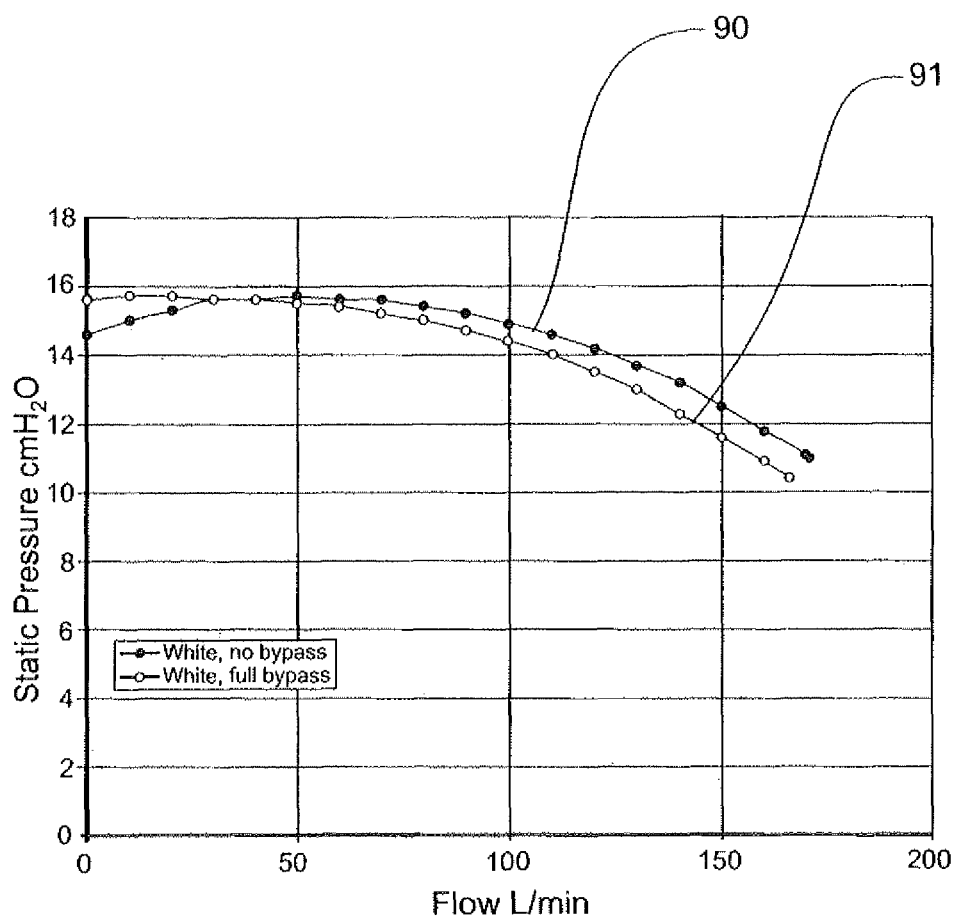
FIG. 19 shows a comparison graph of the pressure plotted against flow for a fan casing with vent holes and a fan casing without vent holes.

FIG. 19 shows an experimental comparison of a fan unit which is very similar to fan unit 20, the experimental fan unit tested in two states: without vent holes (line 90), and with vent holes (line 91). For the un-vented fan unit, it has been found by way of experimentation that surge occurs in that portion of curve 90 where the pressure/flow slope is increasing ('rising') or flat—from zero flow, up to approximately 50 Liters/minute. It can be seen that the line plotted for experimental data gathered from the vented fan unit (line 91) shows a curve that almost exactly parallels line 90 (the curve for the unvented blower), except that it is shifted to the left (along the x-axis). Because curve 91 is shifted to the left, the 'rising' component is removed during normal operating conditions, or lies outside normal operating parameters, and therefore surge is less likely to occur.

Gases Supply Unit Bypass Vent Holes

Figure 11:
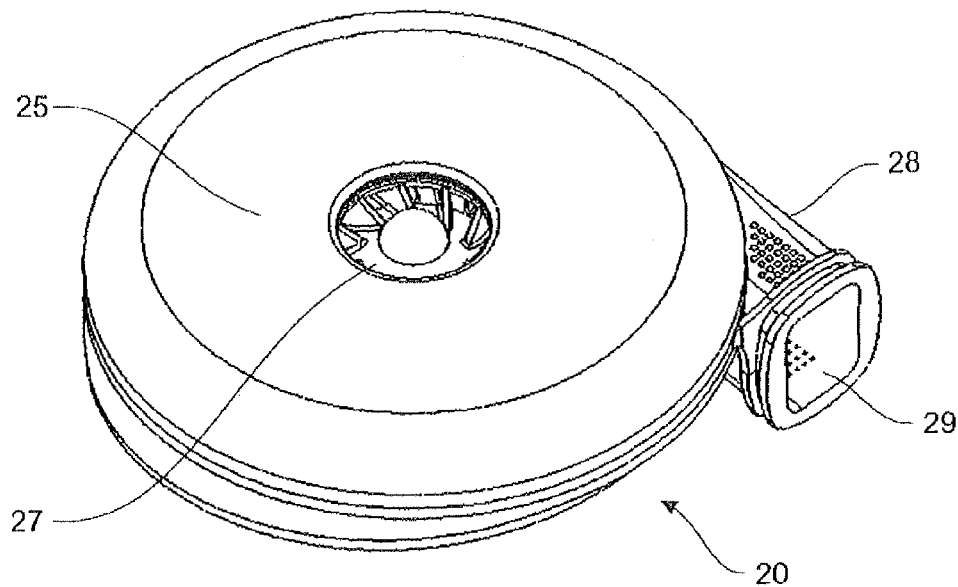
FIG. 11 shows a perspective top view of a fan casing for use with a system that provides heated, humidified air to a user, the casing having an inlet and an outlet passage.
Figure 12:
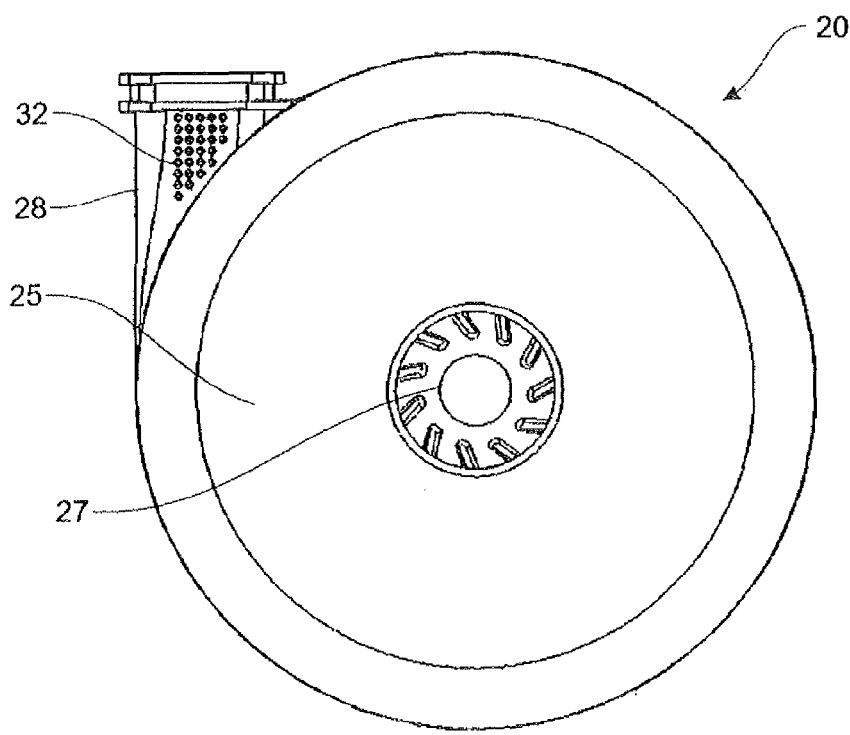
FIG. 12 shows a top view of the fan casing of FIG. 11.
Figure 13:
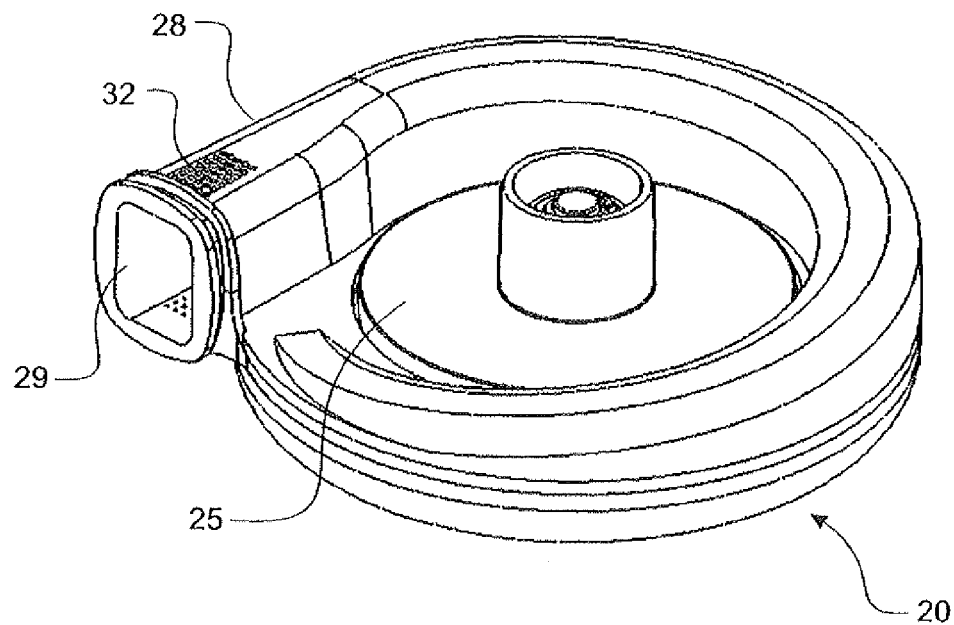
FIG. 13 shows a perspective bottom view of the fan casing of FIGS. 11 and 12.

As can be seen in FIGS. 11 to 16, the preferred form of the fan outlet passage 28 includes vent holes 32 passing through the walls or sides of the fan outlet passage 28. Detail of the vent holes is shown in FIGS. 11 and 12. These vent holes are separate to, or independent of, the fan casing outlet aperture 29 of the fan outlet passage 28. It can be seen that the vent holes 32 will be at an angle to the general overall path of the gases stream. That is, they are arranged at an angle to the general overall path of the gases stream. For a rectangular passage (as in the preferred embodiment), the holes are aligned substantially perpendicular to the general overall path of the gases stream. In the preferred from, the holes are each approximately 0.55 mm in diameter, and have a 10° draft (wider at the external surface of the passage than the internal surface). The draft is beneficial for noise reduction as it allows the flow to escape smoothly—the draft acts as a diffuser, which slows the flow and therefore reduces turbulence and noise. The draft also offers a manufacturing advantage, as it allows the passage to be formed by e.g. injection moulding in one operation including the holes. The holes do not have to be added as a separate manufacturing operation—e.g. by drilling them post-moulding.

When a patient is inhaling, little to no air from the fan unit 20 passes through these holes, as the gases stream will follow the general overall path, or the path of least resistance, from the impeller unit 24 down the passage 28 and through the exit 29. When a user exhales, this can cause throttling in the system, disrupting the smooth flow of the air from the fan unit 20, as described above. The vent holes 32 allow gases to vent from inside the fan outlet passage 28—the outlet passage portion of the fan casing 25. This allows a rate of flow to be maintained through the fan casing 25 that helps to prevent the onset of flow instability. The result is decreased turbulence and therefore less noise. Once a patient finishes exhaling and begins their inhalation phase, one potential cause of throttling in the system is removed. Air ceases to vent through the vent holes 32 and resumes following a path of least resistance from the impeller to the aperture 29, so that substantially all the air from the fan unit 20 passes into the duct 26.

In the preferred form, the blower unit is set by a user to a constant pressure setting, which can be adjusted to different (constant pressure) levels according to the users needs. The flow rate delivered by the CPAP unit or blower unit 8 for any particular constant pressure setting is variable, and depends on an individual user's breathing pattern. Ideally, a CPAP device would deliver a constant pressure for all flow rates. However, in use, for any given pressure setting, the blower unit 8 will actually deliver a variable pressure and flow rate as a user breathes.

The experimental plots of FIG. 19 are for a constant fan speed. The experiment was carried out with a single fan speed setting. The experiment was carried out under laboratory conditions (without a user connected), so the flow rate was substantially constant. The experiment was also carried out with the fan unit alone—i.e. not mounted in a blower shell. It can be seen from the plots that the vented fan unit (line 91) has a static pressure of just under 16 cmH$_2$O, this static pressure substantially constant for a flow rate of between 0-50 Liters/minute. In contrast, it can be seen that the plot for the unvented fan unit includes a rising component for a flow rate between 0-50 Liters/minute.

The preferred form of fan unit is speed adjustable, to provide a range of pressures preferably between approximately 4 cmH$_2$O and 20 cmH$_2$O.

The vent holes should be sized so that the flow through the vent holes matches the outlet flow (flow through the exit aperture 29) at the onset of the stall or surge condition. The total area necessary will depend on the size of the individual holes. Smaller vent holes are preferred as these will have an increased resistance to flow at higher rates of overall flow through the outlet passage 28 (and therefore gases will only vent through the holes when the flow is throttled by back pressure as a user exhales). It has also been found by carrying out testing with vent holes having diameters of between 0.5 mm and 1.5 mm that the holes with smaller diameters tend to be more effective at reducing noise and vibration. For vent holes with larger diameters, sputtering can occur (periodic, random, spitting or popping sounds, or instability), which is undesirable.

In the preferred form, fan casing outlet aperture 29 is larger than the cross-sectional area of any one of the individual vent holes 32 by between approximately two and four, and more specifically substantially three orders of magnitude. The fan casing outlet aperture 29 is larger than the total cross-sectional area of all of the vent holes 32 by between approximately one and two orders of magnitude. Because the fan casing outlet aperture 29 is aligned in substantially the same direction as the general overall path in which the air is already travelling, substantially all of the air from the impeller unit 24 passes along the fan casing outlet passage 28, through the fan casing outlet aperture 29 and into the duct 26.

In the preferred form, the holes 32 of the preferred form have a total cross-sectional area of approximately 16 mm$^2$ to 17 mm$^2$, and are evenly spaced in a generally rectangular pattern. It is preferred that the same number of holes, of the same size, distributed in substantially the same number and the same pattern, are used on the two opposed surfaces, and that the upper and lower opposed surfaces of the fan outlet passage 28 are used, as this offers a manufacturing advantage for the preferred form of fan casing. However, the holes could be placed wherever is convenient, and in whatever pattern is convenient. It should also be noted that different outlet shapes would also be effective—for example, slots or a grid pattern could be used instead. It should also be noted that although a generally rectangular outlet passage has been described, this could be oval, circular, or any other suitable cross-sectional shape. If the passage is circular or oval, for example, the holes could be on two opposed 'sides' of the passage—that is, in two areas which are generally opposed or at generally equal distances from one another around the perimeter of the passage.

Figure 15:
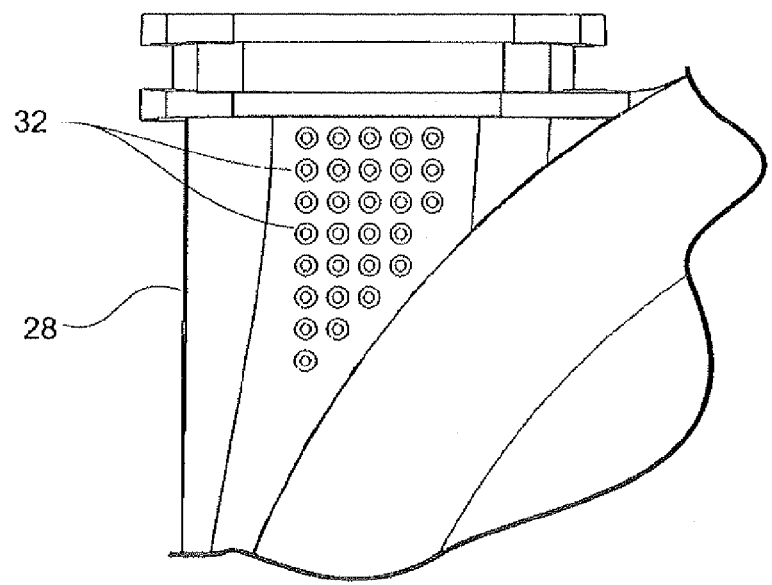
FIG. 15 shows detail of vent holes formed on the top surface of the outlet passage of fan casing of FIGS. 11-14.
Figure 16:
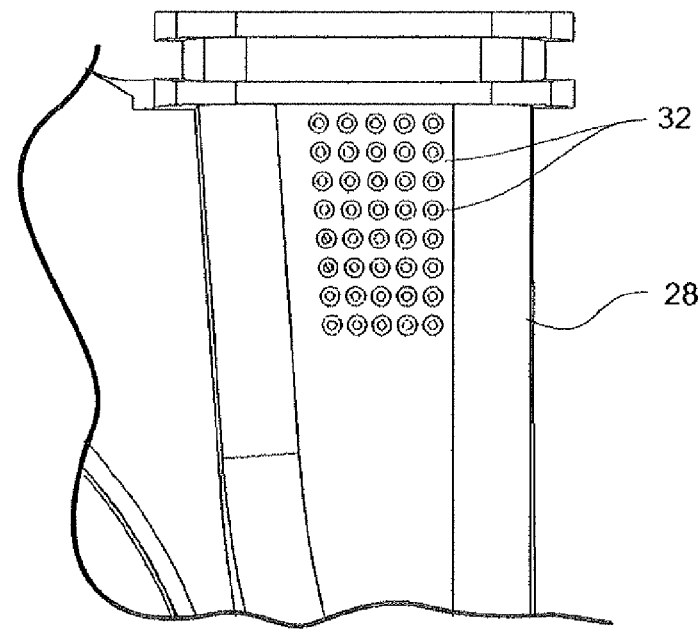
FIG. 16 shows detail of vent holes formed on the lower surface of the outlet passage of fan casing of FIGS. 11-14.

In the most preferred form, the cross-sectional area of the exit aperture 29 is approximately 240 mm$^2$. In the preferred form, the passage 28 has a rectangular cross-section, with the vent holes 32 located on two opposed sides of the rectangular passage. As shown in FIGS. 15 and 16, in the most preferred form, a total of 69 vent holes are formed in the upper and lower surfaces of the passage 28. Each has a diameter on the inside surface of approximately 0.55 mm. The cross-sectional area of each of the holes passing through the inner surface is therefore approximately 0.24 mm$^2$. The total cross-sectional area of the outlet holes is therefore 16.39 mm$^2$ for the most preferred form. It should be noted that this is the most preferred form of the invention. Testing has been carried out using different numbers of vent holes with different diameters. It has been found that the effective total or overall size for the vent holes remains substantially constant and is almost completely independent of the size of each individual hole.

An overall 'bleed', 'diversion' or vent hole cross-sectional area of between 15.5 mm² and 17 mm² is preferred, but it has been found experimentally that the benefits of the invention can be realised with a total vent hole cross-sectional area from as low as approximately 12.0 mm² (seven vent holes, each with a diameter of 1.5 mm). Tests with vent holes having diameters of 0.55 mm, 0.75 mm, 1.00 mm, 1.25 mm and 1.5 mm have also been carried out. The number of holes of each diameter needed to prevent excessive mechanical noise or 'rumble' was varied (although it should be noted that this was a subjective test, and that no fixed parameter was measured to determine a suitable noise level). The number of holes necessary to prevent rumble for each of the different diameters is as follows: 56 (0.55 mm), 28 (0.75 mm), 17, (1.00 mm), 11 (1.25 mm), and 7 (1.5 mm).

As noted above, the test equipment was slightly different from the preferred form of fan casing 25. The number and size of holes in the most preferred form was decided as 69 holes, each of 0.55 mm diameter.

This testing indicates that the benefits of the invention can be realised with a single vent hole having a cross-sectional area in the region of between 12.0 mm² to 17 mm². Although it has been found that a pattern of small holes each having an area of approximately 0.24 mm² is more effective than using one large hole, the invention can still be realised using one larger hole, or a smaller number of larger holes. This will still produce the same reduction in throttling side effects, as gases can vent in a throttle condition, and flow through the impeller can be maintained. However, there can be other undesirable side-effects from using large holes (rather than a larger number of smaller holes with the same cross-sectional area). For example, gases will vent mote easily through the holes during the inspiratory phase as well as the expiratory phase. This leads to a lower overall system pressure, and reduces the effectiveness of the holes in minimising back pressure effects as a certain amount of gas will already be flowing through them when a user starts to exhale. Also, as noted above, it has been found that smaller holes tend to be more effective at reducing noise and vibration. For vent holes with larger diameters, sputtering can occur (periodic spitting or popping sounds), which is undesirable.

Although round vent holes have been described, differently shaped holes with the same area could be used if this is preferred. A mix of holes of different shapes and sizes could also be used if this is preferred, or if this configuration would be beneficial in certain situations.

The invention as outlined above is beneficial in reducing noise and vibration in assisted breathing systems.

I claim:

1. A fan unit that in use forms part of a gases supply unit suitable for use as part of a system for providing heated humidified gases to a user, said fan unit comprising: a casing having an inlet aperture and an outlet passage, said outlet passage having an exit aperture, and at least one vent hole independent of said exit aperture and arranged at an angle to a path of a gases stream through said outlet passage; and a fan located inside said casing and adapted for connection to a motor to drive rotation of said fan in use so that in use said fan draws gases into said casing via said inlet aperture and forces said gases out of said casing via said outlet passage as said gases stream, said outlet passage and said at least one vent hole configured so that, if said outlet of said outlet passage is substantially blocked, a flow in use through said at least one vent hole matches a flow through said outlet passage at which an onset of surge would occur in a substantially blocked outlet passage without a vent hole or holes.

2. A fan unit as claimed in claim 1 wherein said exit aperture is larger than a cross-sectional area of said at least one vent hole by approximately three orders of magnitude.

3. A fan unit as claimed in claim 1 wherein said at least one vent hole comprises two or more vent holes and said exit aperture is larger than a total cross-sectional area of said two or more vent holes by approximately one to two orders of magnitude.

4. A fan unit as claimed in claim 1 wherein said angle of said at least one vent hole to said path of said gases stream is substantially perpendicular.

5. A fan unit as claimed in claim 1 wherein said outlet passage has a plurality of said at least one vent holes.

6. A fan unit as claimed in claim 5 wherein said outlet passage comprises two opposed sides and said vent holes are located on said two opposed sides of said outlet passage.

7. A fan unit as claimed in claim 6 wherein substantially the same number of vent holes are formed on each of said two opposed sides.

8. A fan unit as claimed in claim 5 wherein said at least one vent holes number between 65 and 75.

9. A fan unit as claimed in claim 5 wherein each of said vent holes is substantially the same size as the others of said vent holes.

10. A fan unit as claimed in claim 5 wherein said exit aperture has a cross-sectional area of substantially between 210 and 270 mm².

11. A fan unit as claimed in claim 9 wherein a cross-sectional area of each of said vent holes on an inner surface of said outlet passage is substantially between 0.22 mm² and 0.26 mm².

12. A fan unit as claimed in claim 9 wherein a total cross-sectional area of said vent holes on an inner surface of said outlet passage is substantially between 15.00 mm² and 17.00 mm².

13. A fan unit as claimed in claim 5 wherein said vent holes are formed with a draft of substantially between 5° and 15°.

14. A fan unit as claimed in claim 13 wherein said vent holes are formed with a draft of 10°.

15. A fan unit as claimed in claim 5 wherein said casing has a generally circular form and said outlet passage is tangential to said casing.

16. A fan unit as claimed in claim 15 wherein said exit aperture has a generally rectangular cross-section.

17. A fan unit as claimed in claim 16 wherein said inlet aperture is located on a lower face of said casing in use.

18. A fan unit as claimed in claim 17 wherein said inlet aperture is located generally centrally on said casing.

19. A fan unit as claimed in any one of claims 15 to 18 wherein said fan is an impeller unit.

20. A fan unit as claimed in claim 19 wherein said impeller unit has a spindle, adapted for connection to a motor in use to drive said impeller unit, said spindle passing out of a bottom of said casing.

21. A housing for a fan unit that in use forms part of a gases supply unit suitable for use as part of a system for providing heated humidified gases to a user, said housing comprising: an outer casing having an inlet aperture and an outlet passage, said outlet passage having an exit aperture and at least one vent hole, said at least one vent hole independent of said exit aperture and arranged at an angle to an overall path of a gases stream passing along said outlet passage in use, said outer casing adapted to enclose a fan in use, and wherein said outlet passage and said at least one vent hole are configured so that, if in use an outlet of said outlet passage is substantially blocked, a flow through said at least one vent hole matches a flow through said outlet passage at which an onset of surge would occur in a substantially blocked outlet passage without a vent hole or holes.

22. A housing for a gases supply unit that in use forms part of a system for providing heated humidified gases to a user and that is adapted to in use provide a pressurised gases stream, said housing comprising: an enclosing external shell that encloses and forms part of a gases supply unit, said enclosing external shell having an atmospheric inlet adapted to allow gases from atmosphere to enter said enclosing external shell in use, and a humidifier inlet aperture adapted to allow said pressurised gases stream to exit said enclosing external shell, said enclosing external shell further comprising an internal recess adapted to hold a fan casing in use, an outlet duct, having an outlet end adjacent to and fluidically connected to said humidifier inlet aperture, and an inlet end, a passage that in use fluidically connects an outlet of said fan casing and said inlet end of said outlet duct, said passage having at least one vent hole, arranged at an angle to an overall path of said pressurized gases stream through said passage, said passage and said at least one vent hole configured so that, if said pressurized gases stream cannot pass freely along said passage, a flow in use through said at least one vent hole matches a flow through said passage at which an onset of surge would occur in a substantially blocked outlet passage not having a vent hole or holes.

23. A housing for a gases supply unit as claimed in claim 22 wherein said passage is formed as an integral part of said housing.

24. A housing for a gases supply unit as claimed in claim 22 wherein said passage is formed as a separate item to said enclosing external shell, and is connected to said enclosing external shell in use.

25. A housing for a gases supply unit as claimed in claim 22 wherein said passage is located and arranged in said enclosing external shell so that in use gases from said fan enter said passage substantially at a tangent to said fan.

26. A gases supply unit that in use forms part of a system for providing heated humidified gases to a user, said gases supply unit comprising: a housing having an external shell that encloses and forms part of said gases supply unit, said external shell having an atmospheric inlet adapted to allow gases from atmosphere to enter said external shell in use, and a humidifier inlet aperture adapted to allow a pressurised gases stream to exit said external shell, and an internal recess adapted to hold a fan unit, said fan unit located in said internal recess, said fan unit having an external fan casing with an inlet aperture and an outlet aperture, and a fan located inside said external fan casing, said fan unit adapted to draw air into said gases supply unit through said atmospheric inlet and provide a pressurised gases stream through said outlet aperture in use, a motor located within said external shell and adapted for connection to said fan unit to drive said fan in use, an outlet duct having an outlet end adjacent to and fluidically connected to said humidifier inlet aperture and an inlet end, a passage that in use fluidically connects said outlet of said external fan casing and said inlet end of said outlet duct, said passage having at least one vent hole arranged at an angle to an overall path of said gases stream through said passage, wherein said passage and said at least one vent hole are configured so that, if said gases pressurized stream cannot pass freely along said passage, a flow in use through said at least one vent hole matches a flow through said passage at which an onset of surge would occur in a substantially blocked outlet passage not having a vent hole or holes.

27. A housing for a gases supply unit as claimed in claim 26 wherein said passage is formed as an integral part of said housing.

28. A housing fir a gases supply unit as claimed in claim 26 wherein said passage is formed as a separate item to said external shell, and is connected to said external shell in use.

29. A housing for a gases supply unit as claimed in claim 26 wherein said passage is located and arranged in said external shell so that in use gases from said fan enter said passage substantially at a tangent to said fan.

30. A medical breathing system suitable for supplying heated humidified gases to a user, the system comprising: a gases supply unit adapted to provide a pressurised gases stream, a humidifier chamber fluidically connected to said gases supply unit in use so that said gases stream can pass into and through said humidifier chamber, said humidifier chamber containing a volume of water that in use is heated to heat and humidify said gases stream as said gases stream passes through said humidifier chamber, a patient interface adapted to provide said heated humidified gases stream to a user, said patient interface including a conduit to transport said heated humidified gases from said humidifier chamber to said user, said gases supply unit comprising: a housing having an external shell that encloses and forms part of said gases supply unit, said external shell having an atmospheric inlet adapted to allow gases from atmosphere to enter said external shell in use, a humidifier inlet aperture adapted to allow said pressurised gases stream to exit said external shell, and an internal recess adapted to hold a fan unit, a fan unit located in said internal recess, said fan unit having an external fan casing with an inlet aperture and an outlet aperture, a fan located inside said external fan casing, said fan unit adapted to draw air into said external shell through said atmospheric inlet and provide said pressurised gases stream through said outlet aperture in use, a motor located within said external shell and adapted for connection to said fan unit to drive said fan in use, an outlet duct having an outlet end adjacent to and fluidically connected to said humidifier inlet aperture and an inlet end, a passage that in use fluidically connects an outlet of said external fan casing and said inlet end of said outlet duct, said passage having at least one vent hole arranged at an angle to an overall path of said pressurized gases stream through said passage, wherein said passage and said at least one vent hole are configured so that, if said pressurized gases stream cannot pass freely along said passage, a flow in use through said at least one vent hole matches a flow through said passage at which an onset of surge would occur in a substantially blocked outlet passage not having a vent hole or holes.

31. A medical breathing system as claimed in claim 30 wherein said external shell is further configured to at least partially enclose said humidifier chamber in use.

32. A medical breathing system as claimed in claim 30 or claim 31 wherein said external shell and said humidifier chamber are mutually configured so that said outlet aperture can mate directly with an inlet port to said humidifier chamber in use.

* * * * *